United States Patent [19]

Davis

[11] 4,250,167

[45] Feb. 10, 1981

[54] METHODS FOR REDUCING CALCIUM DEPOSITS

[76] Inventor: Elgan A. Davis, 7103 Marconi St., Huntington Park, Calif. 90255

[21] Appl. No.: 943,732

[22] Filed: Sep. 19, 1978

[51] Int. Cl.$^3$ .............................................. A61K 37/48
[52] U.S. Cl. ...................................... 424/94; 424/337
[58] Field of Search ................................. 424/94, 337

[56] References Cited

U.S. PATENT DOCUMENTS

| | | | |
|---|---|---|---|
| 3,551,554 | 12/1970 | Herschler | 424/89 |
| 3,627,875 | 12/1971 | Fellonneau | 424/94 |

OTHER PUBLICATIONS

Chemical Abstracts 64:7241h (1966) (Innerfield et al.).
Chemical Abstracts 65:9269h (1966) (Innerfield).
Schneider et al.–Chem. Abst. vol. 66, 1967 p. 112,230u.
Collignon et al.–Chem. Abst. vol. 84, 1976 p. 15,937u.
Merck Index–Ninth edition (1976), p. 433, article 3,249.

*Primary Examiner*—Leonard Schenkman
*Attorney, Agent, or Firm*—William P. Green

[57] ABSTRACT

An inert calcium deposit located beneath the surface of the skin is reduced by application to the outside of the skin of a composition comprising dimethyl sulfoxide and papain, the enzyme found in papaya. The dimethyl sulfoxide transports the enzyme through the skin toward the location of the inert calcium, minutely dissolves the inert calcium and through the natural body circulatory processes removes the liquified calcium from the area and purges it from the body.

The dimethyl sulfoxide penetrates the body without disturbing normal body functions and the natural herbal enzyme papain then performs the function of dissolving inert calcium.

10 Claims, No Drawings

METHODS FOR REDUCING CALCIUM DEPOSITS

BACKGROUND OF THE INVENTION

The invention relates to improved compositions and methods for reducing, and preferably removing completely, abnormal inert deposits of calcium located beneath the skin of an animal or other living organism, by liquifying or dissolving the calcium and then utilizing the natural circulatory process to remove the irritating calcium deposits from joint or tissue areas without the necessity for surgical treatment or hypodermic injections which might cause further damage.

One of the physical ailments very frequently encountered in race horses is the development of inert calcium spurs, lumps or other calcium deposits in one or more of the legs of the horse, causing irritation and a reduction in the mobility of the horse and/or great pain as the horse attempts to run. Such inert calcium deposits reduce drastically the speed at which the horse can run, and usually result in the shortening of the racing life of the horse. Inert calcium deposits can also similarly adversely affect other animals, including of course humans in which arthritic ailments cause very disconcerting and painful reduction in mobility.

Numerous attempts have been made in the past to temporarily or permanently attack such inert calcium deposits, but I am not aware of any which has enjoyed any substantial success.

DESCRIPTION OF THE INVENTION

The purpose of the present invention is to provide a composition and method of treatment which will overcome the above discussed problems of inert calcium deposition in animals and other organisms, and will reduce or completely remove abnormal inert calcium deposits from bones, joints, and other portions of a body in a manner freeing the body for movement through an increased range and with reduced pain, and preferably no pain at all if the treatment is continued for a period of time.

The composition includes as one ingredient papain, i.e. the enzyme or enzymes extracted from Carica papaya, such as the product sold under the trade name "Papase" by Warner-Chilcott Laboratories, a division of Warner-Lambert Company, Morris Plains, N.J., 07950. The papain will not affect bone calcium within a living body but does dissolve inert calcium. This ingredient also reduces tumescence, aids the flow of blood to affected areas, and assists the natural body circulatory process in bathing those areas. A second ingredient intermixed with the papain is dimethyl sulfoxide, whose chemical formula is $(CH_3)_2SO$, and which is commonly known by the abbreviation DMSO. Dimethyl sulfoxide is an organic compound which may be derived from lignin, a constituent of wood, and at room temperature takes the form of a colorless liquid. The chemical has a capacity for penetrating living tissues, and for carrying an intermixed substance through the skin of an animal or other living organism.

The papain is normally supplied in a dry solid form, and in forming the present composition is ground or otherwise broken down to a fine powder or fine particulate form, and then intermixed intimately with the liquid dimethyl sulfoxide to form an essentially uniform composition. It is contemplated that in some instances additives may be utilized in conjunction with these two primary ingredients, such as for example Vitamin A to facilitate healing, but preferably the papain and dimethyl sulfoxide together form the major portion of the composition, and in some instances the composition may consist entirely of these two ingredients. The dimethyl sulfoxide and papain may be employed in varying proportions, desirably between about 200,000 and 1,000,000 Warner-Chilcott Units of papain to one pint of dimethyl sulfoxide. One Warner-Chilcott unit is that quantity of proteolytic enzymes extracted from carica papaya which will clot 2.64 microliters of milk substrate in 2 minutes at 40° C. The ultimate composition of the present invention is itself a fairly thin liquid easily applicable to the skin of an animal or the like, preferably by spraying directly onto the skin.

Before application of the composition, the skin is desirably washed or otherwise cleaned thoroughly, preferably with soap and water, then rinsed well with water and allowed to air dry. If the deposit to be treated is on the ankle or leg of a horse, or other animal having relatively heavy hair, the hair may be clipped at a location opposite the abnormal calcium deposit, and/or be brushed before being cleaned and treated with the composition.

The affected area is treated in this way regularly, desirably at least about once a day and preferably twice a day. On each application, enough of the liquid composition is sprayed onto or otherwise applied to the skin to attain a reasonably wet condition of the skin. Preferably, no bandage is applied to the area, but instead the area is left exposed to the atmosphere as the composition dries and penetrates through the skin and to the location of the calcium deposit. Such twice daily treatment may be continued for several days or weeks, say 10–12 weeks, with gradual reduction in size and preferably ultimate complete removal of the calcium deposit as the treatments progress.

The dimethyl sulfoxide carries the intimately intermixed papain into and in most instances entirely through the skin and to the location of the calcium deposit, at which point the papain liquifies the calcium and progressively reduces the size of the deposit. As the abnormal liquified calcium is removed from a joint area, the joint becomes free for increased movement without pain; and as the calcium is liquified and removed from other areas it similarly decreases pain caused by movement. All of this is accomplished without surgically cutting through the skin or otherwise disturbing the natural protection afforded by the skin.

The following specific examples are given of particular compositions and treatment methods which have been utilized on a number of race horses afflicted with calcium deposits.

EXAMPLE 1

A female thoroughbred race horse had developed calcium deposits in one of her front ankles to the extent that these deposits caused obvious pain to the animal and interfered with her normal racing ability. The pain caused her to race more slowly than she otherwise would, and without the present treatment would have rendered her useless for further racing. Before treatment, lumps of calcium could be felt in her ankle, on the anklebone and at the joint. There should have been no calcium deposits at the locations at which these lumps could be felt. This condition is one normally described as the results of a "bowed" ankle. It is estimated that the lumps were approximately 3 to 5 millimeters in size.

The composition utilized on this horse consisted only of papain and methyl sulfoxide intimately intermixed to form a uniform liquid composition. More particularly, the papain ingredient was the product sold as "Papase" by Warner-Chilcott Laboratories, and described as proteolytic enzymes of Carica papaya, while the methyl sulfoxide was the product sold under that name by Mallinckrodt, Inc. of St. Louis, Missouri. The proportions of the two ingredients were 300,000 Warner-Chilcott Units of the enzymes to one pint of methyl sulfoxide.

The horse was treated twice a day, morning and night, for 12 weeks. At the outset, the hair was clipped from the horse's ankle in the vicinity of the calcium deposits, and on each treatment the skin was first brushed, then washed thoroughly with soap and water, rinsed well with water, and then allowed to dry thoroughly in air. The mixture was then sprayed onto the ankle at and near the location of the calcium deposits, and in a quantity sufficient to give the ankle a reasonably wet appearance, following which the ankle was allowed to dry without being bandaged.

As the treatments progressed, it was easy to feel through the skin of the horse's ankle that the lumps were gradually decreasing in size, and after 12 weeks of treatment the lumps had disappeared completely. The horse no longer showed signs of pain as it had at the outset, and could run freely and race more successfully than before treatment.

EXAMPLE 2

A quarterhorse stud in the roping class had a completely immobilized left front ankle, in which it showed no capacity for movement whatever and evidenced great pain. As felt through the skin, abnormal deposits of calcium appeared to be almost solid at the ankle joint, the condition being so bad that it could easily be seen from a distance, and gave the left front ankle a swollen poorly shaped appearance obviously different from the right ankle of the same animal.

The same compositon described in connection with Example 1 above, including 300,000 Warner-Chilcott Units of papain per pint of dimethyl sulfoxide, was utilized twice a day, morning and night, for six weeks on this animal, with the same treatment procedure discussed in Example 1. After that six week period, the left front ankle which had been completely immobile now had substantial mobility, the animal did not stumble as he had at the commencement of the treatment, and the size of the ankle had reduced visibly and substantially. At the beginning of the treatment, the horse was in such poor condition that it could not be worked more than approximately one day in four. After six weeks of treatment, however, the horse could be worked every day with no difficulty or evidence of pain.

EXAMPLE 3

A female thoroughbred horse had a condition known as "shin buck", in which minute calcium deposits were present in the thin layer of skin in the front of the leg and caused extreme pain readily evident from the manner in which the horse reacted after exercise and upon movement of the legs. Because of the pain which accompanied movement of the leg, the horse could not run at all.

A composition utilized in treating this horse consisted of 500,000 Warner-Chilcott Units of papain (the product Papase of Warner-Chilcott Laboratories) per pint of dimethyl sulfoxide. Also contained in the composition were 200,000 units of injectable formula Vitamin A to facilitate healing. The horse was treated with this composition twice a day, morning and night, for two weeks. At the commencement of the series of treatments, the hair was clipped from the affected portion of the horse's leg, and on each treatment the previously discussed washing, rinsing and drying procedures were followed. At the end of the two week period, the horse appeared completely cured, it could walk and run well with no evidence whatever of soreness, and the "shin buck" was made sound.

EXAMPLE 4

The horse involved in this example had developed a calcium spur on one ankle, which spur could be seen in an X-ray of the ankle. The spur was broken off of the bone on which it originally had formed. The composition described in Example 3 was sprayed onto the skin of the ankle at a location opposite the spur twice a day, morning and night, for 12 weeks, after which X-ray examination showed that the spur had completely disappeared. The clipping and cleaning procedures were of course followed in this example as on the other horses described above. After the treatment, the horse, which had previously been in great pain and completely unable to race, was again able to and did race, and was a winner in at least one race of which I am aware.

While certain specific embodiments of the present invention have been disclosed as typical, the invention is of course not limited to these particular forms, but rather is applicable broadly to all such variations as fall within the scope of the appended claims.

I claim:

1. The method of reducing a deposit of inert calcium beneath the skin that comprises:
    applying to the skin a composition containing intermixed effective amounts of dimethyl sulfoxide and papain;
    conveying said papain into the skin and to the location of the calcium deposit by action of said dimethyl sulfoxide; and
    reducing the calcium deposit by action of said papain.

2. The method as recited in claim 1, in which said papain is present in the proportion of between about 200,000 and 1,000,000 Warner-Chilcott Units per pint of dimethyl sulfoxide.

3. The method as recited in claim 1 in which said papain is present in the proportion of approximately 300,000 Warner-Chilcott Units per pint of dimethyl sulfoxide.

4. The method as recited in claim 1, including applying said composition to the outside of the skin at intervals over an extended period of time to reduce the calcium deposit progressively.

5. The method as recited in claim 2, including applying said composition to the outside of the skin at least once daily for a period of time to reduce the calcium deposit progressively.

6. The method of reducing an inert calcium deposit in the leg of a horse that comprises:
    applying to the outside of the skin of the horse's leg at a location near the calcium deposit a composition containing intermixed effective amounts of dimethyl sulfoxide and papain;
    transporting the papain into the skin and to the location of the calcium deposit by action of said dimethyl sulfoxide; and reducing the calcium deposit by the action of the papain.

7. The method as recited in claim 6, in which said composition consists essentially of said dimethyl sulfoxide and said papain.

8. The method as recited in claim 6, in which said composition consists essentially of said dimethyl sulfoxide and said papain, and in a proportion of between about 200,000 and 1,000,000 Warner-Chilcott Units of papain to one pint of dimethyl sulfoxide.

9. The method as recited in claim 6, in which said composition is applied by spraying it onto the skin.

10. The method as recited in claim 6, including clipping hair from the horse's leg at the location of the calcium deposit, and applying the composition to the skin at that location.

* * * * *